(12) United States Patent
Jose et al.

(10) Patent No.: US 11,879,894 B2
(45) Date of Patent: Jan. 23, 2024

(54) BIFUNCTIONAL PHOTOACTIVABLE FLUORESCENT LIPID PROBES FOR PROXIMITY LABELLING-BASED IDENTIFICATION OF MEMBRANE-ASSOCIATED PROTEINS

(71) Applicant: INDIAN INSTITUTE OF SCIENCE EDUCATION AND RESEARCH, Pune (IN)

(72) Inventors: Gregor Jose, Pune (IN); Thomas Pucadyil, Pune (IN)

(73) Assignee: Indian Institute of Science Education and Research, Pune (IN)

( * ) Notice: Subject to any disclaimer, the term of this patent is extended or adjusted under 35 U.S.C. 154(b) by 622 days.

(21) Appl. No.: 16/891,373

(22) Filed: Jun. 3, 2020

(65) Prior Publication Data
US 2020/0386764 A1    Dec. 10, 2020

(30) Foreign Application Priority Data

Jun. 4, 2019   (IN) .............................. 201921022074

(51) Int. Cl.
*G01N 33/58*   (2006.01)
*G01N 33/68*   (2006.01)

(52) U.S. Cl.
CPC ....... *G01N 33/582* (2013.01); *G01N 33/6803* (2013.01); *G01N 2405/00* (2013.01)

(58) Field of Classification Search
CPC ............. G01N 33/582; G01N 33/6803; G01N 2405/00
See application file for complete search history.

(56) References Cited

PUBLICATIONS

Xia et al. Photoactivatable Lipid Probes for Studying Biomembranes by Photoaffinity Labeling. Chem. Rev. 2013, vol. 113, pp. 7880-7929. (Year: 2013).*
Demchenko et al. Introduction to Fluorescence Probing of Biological Membranes. Methods in Molecular Biology, 2015, vol. 1232, pp. 19-43. (Year: 2015).*

* cited by examiner

*Primary Examiner* — Shafiqul Haq
(74) *Attorney, Agent, or Firm* — Banner & Witcoff, Ltd.

(57) ABSTRACT

This invention discloses bi-functional photoactivable fluorescent lipid probes for proximity labelling-based identification of membrane-associated proteins, and synthesis thereof. The photoactivable fluorescent lipid probe include a lipid moiety, a fluorophore, and a photoactivable moiety; where the fluorophore and the photoactivable moiety are covalently attached to the lipid moiety.

7 Claims, 6 Drawing Sheets

Theoretical m/z = 976.5917
Experimental m/z = 976.5899

Theoretical m/z = 1244.5893
Experimental m/z = 1244.5890

BIFUNCTIONAL PHOTOACTIVABLE FLUORESCENT LIPID PROBES FOR PROXIMITY LABELLING-BASED IDENTIFICATION OF MEMBRANE-ASSOCIATED PROTEINS

FIELD OF INVENTION

This invention relates to a novel bi-functional photoactivable fluorescent lipid probes for proximity labelling-based identification of membrane-associated proteins, and synthesis thereof.

BACKGROUND AND PRIOR ART OF THE INVENTION

Peripherally bound membrane proteins, referred to herein as membrane-associated proteins (MAPs), are an important class of molecules found in all biological systems (Saliba et al. (2015) Nat. Rev. Mol. Cell Biol. 16:753-61). MAPs are involved in a variety of biological phenomena that range from cell signalling, cell-cell communication, host immunity, host-pathogen interaction and maintenance of cell and organelle identity. Understanding each of these biologically important phenomena necessitates the accurate determination of the complete repertoire of tissue-, cell-, or organelle-specific MAPs or analyse if a protein of interest (POI) can bind membranes, which is a challenging task.

Current methods to analyse membrane-binding of proteins include; (a) density gradient-based fractionation and/or high-speed sedimentation of native membranes or membrane-mimetic systems such as liposomes, (b) fluorescence imaging-based localization of POI(s) fused to an intrinsically fluorescent protein or covalently labelled with a fluorophore to specific cellular organelles or membrane-mimetic systems such as liposomes, (c) lipid overlay assays using dot-blots to determine specific lipid binding of MAPs, (d) binding analysis with purified proteins to liposomes using sophisticated methods such as surface plasmon resonance or NMR, and (e) in silico approaches based on homology to existing MAPs. However, each one of the above methods to analyse membrane-binding of proteins has certain drawbacks, as detailed below.

Sedimentation-based assays suffer from drawbacks such as; (a) the need for tissue or cell lysis which could interfere with native distribution of POIs, (b) the inability to distinguish between direct membrane binding and binding via a secondary membrane-localized POI, (c) requirement for an ultracentrifuge to separate unbound proteins from the POI in the sample.

Fluorescence imaging-based localization is tedious and suffers from the possibility that covalent modification of proteins with fluorophores or tagging with an intrinsically fluorescent protein could compromise native functions and/or distribution of the POI.

Lipid overlay assays using dot-blots have lipids displayed on a solid surface and not in their native membrane environment.

Surface plasmon resonance- or NMR-based methods require the use of sophisticated and expensive equipments.

In silico-based approaches have limited predictive capacities. The methods or algorithms of the silico-based approaches are unable to predict if POI displays peripheral association with membranes.

Further, there is ample literature available on provision of various probes including lipid-based probes for identification of protein-lipid interactions or for binding to bioactive substances, as detailed herein below.

WO2017074937 discloses an activable and taggable lipid probe that finds use in the identification of protein-lipid interactions. The activable moiety is a photoactivable diazirine ring at the headgroup and the taggable moiety is a clickable group comprising of a terminal alkyne at the tail of phosphatidylethanolamine (PE).

U.S. Pat. No. 5,405,766A discloses a method for conjugation of phosphatidylethanolamine (PE) to NHS-activated solid supports, suitable for binding to bioactive substances as well as to modified solid supports.

Delfino et al. (J. Am. Chem. Soc. (1993) 115:3458-3414) discloses a photochemical probe bis-phosphatidylethanolamine (trifluoromethyl1) phenyldiazirie (DIPETPD) wherein a non-fluorescent lipid bis-phosphatidylethanolamine contains a photoactivable diazirine group in the fatty acyl chain.

Ge et al. (RSC Adv. (2018) 8:29428) list various lipid probes with a diazirine group and alkyne handle for studying lipid-protein interactions.

Harter et al. (Biochemistry (1988) 27:1856-1864) describes a bi-functional phospholipid probe with a photoactivable diazirine moiety at the headgroup of a radioactive phospholipid.

Haberkant et al. (Angew. Chem. Int. Ed. (2013) 52:4033-4038) report a bi-functional fatty acid probe which contains a diazirine moiety at the headgroup and a clickable terminal alkyne at the tail.

Haberkant et al. (ACS Chem. Biol. (2016) 11:222-230) describe a bi-functional sphingosine molecule with a diazirine moiety and an alkyne handle at the fatty acyl chain.

Wang et al. (Angew. Chem. Int. Ed. (2017) 56:5829-5833) describe a phosphatidylcholine probe with an alkyne tag as the headgroup and a diazirine group in the fatty acyl chain.

Fluorescence-based approaches offer sensitivity and versatility for detecting many types of intermolecular interactions but none of the previously reported probes for detecting MAPs are intrinsically fluorescent. In the light of there being no effective lipid probes available for proximity labelling-based identification of membrane-associated proteins, it is necessary to develop bi-functional photoactivable fluorescent lipid probe for accurate determination of the complete repertoire of tissue-, cell- or organelle-specific MAPs or if POI is a MAP.

OBJECTIVES OF THE INVENTION

In the light of the foregoing, the primary objective of the present invention is to synthesize photoactivable fluorescent phospholipid probes which when incorporated into liposomes can crosslink with any MAP bound to these liposomes that can be detected on an SDS-PAGE and identified using mass spectrometric approaches.

SUMMARY OF THE INVENTION

As discussed above, fluorescence-based approaches offer sensitivity and versatility for detecting many types of intermolecular interactions but none of the previously reported probes for detecting MAPs are intrinsically fluorescent. In light of the non-availability of fluorescent lipid probes to directly evaluate protein binding to membranes, it is necessary to develop such bi-functional fluorescent lipid probes.

Accordingly, the present invention provides photoactivable fluorescent lipid probes, their synthesis and methods of use thereof. In particular, the probes described in the present invention find use in the identification and analysis of MAPs. These lipid probes, when incorporated into liposomes, can cross-link with any MAP bound to liposomes which can be detected by fluorescence imaging of proteins resolved using SDS-PAGE. This methodology is herein after referred as Proximity-based Labelling of Membrane-Associated Proteins (PLiMAP).

In line with the above, in an aspect, the present invention provides photoactivable fluorescent lipid probes, which comprises (a) lipid moiety, (b) fluorophore, and (c) photoactivable moiety; wherein the fluorophore and the photoactivable moiety is attached covalently with the lipid moiety.

According to an aspect, the photoactivable moiety is a diazirine group or sulfo-diazirine group.

According to another aspect, the fluorophore moiety is a dipyrrometheneboron difluoride group.

More specifically, the fluorophore moiety according to the invention is selected from the group consisting of (4,4-difluoro-1,3-dimethyl-5-(4-methoxyphenyl)-4-bora-3α,4α-diaza-s-indacene-2-propionyl)amino group or 4,4-Difluoro-1,3,5,7-Tetramethyl-4-Bora-3a,4a-Diaza-s-Indacene group.

According to one aspect, the photoactivable moiety is directly connected to the lipid moiety.

According to another aspect, the photoactivable moiety is connected to the lipid moiety through a disulfide bond, which can be released from the lipid by reducing the disulfide bond.

DETAILED DESCRIPTION OF THE INVENTION

Figure 1:
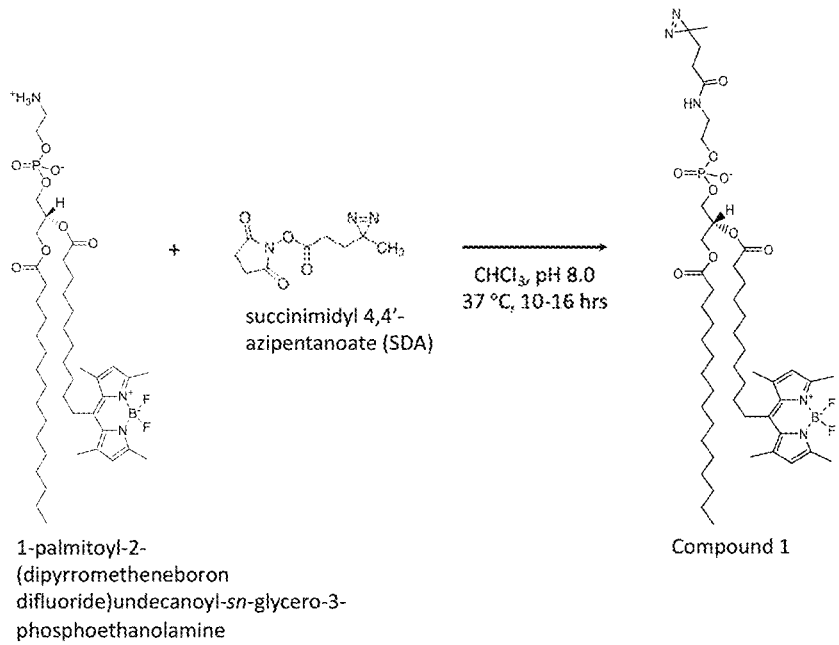
FIG. 1: Synthesis scheme for Compound 1.

The invention will now be described in detail in connection with certain preferred and optional embodiments, so that various aspects thereof may be more fully understood and appreciated.

In line with the above, the present invention provides photoactivable fluorescent lipid probes, which comprises (a) lipid moiety, (b) fluorophore, and (c) photoactivable moiety; wherein the fluorophore and the photoactivable moiety is attached covalently with the lipid moiety.

According to an embodiment, the photoactivable moiety is a diazirine group or sulfo-diazirine group.

According to another embodiment, the fluorophore moiety is a dipyrrometheneboron difluoride group.

According to an embodiment, photoactivable fluorescent lipid probes means and includes the fluorescent lipid probes that gets activated with light of a specific wavelength, intensity and duration, for example, UV light etc.

More specifically, the fluorophore moiety according to the invention is selected from the group consisting of (4,4-difluoro-1,3-dimethyl-5-(4-methoxyphenyl)-4-bora-3α,4α-diaza-s-indacene-2-propionyl)amino group or 4,4-difluoro-1,3,5,7-tetramethyl-4-bora-3a,4a-diaza-s-indacene group.

According to one embodiment, the photoactivable moiety is directly connected to the lipid moiety.

According to another embodiment, the photoactivable moiety is connected to the lipid moiety through a disulfide bond, which can be released from the lipid by reducing the disulfide bond.

According to the present invention, the photoactivable fluorescent lipid probe is selected from the group consisting of;

a) 1-palmitoyl-2-(dipyrrometheneboron difluoride) undecanoyl-sn-glycero-3-phosphoethanolamine conjugated to a diazirine moiety (compound 1)

b) 1-oleoyl-2-(6-((4,4-difluoro-1,3-dimethyl-5-(4-methoxyphenyl)-4-bora-3α,4α-diaza-s-indacene-2-propionyl) amino)hexanoyl)-sn-glycero-3-phosphoethanolamine conjugated to a diazirine moiety (compound 2)

c) 1-palmitoyl-2-(dipyrrometheneboron difluoride) undecanoyl-sn-glycero-3-phosphoethanolamine conjugated to sulfo-diazirine moiety (compound 3)

d) 1-oleoyl-2-(6-((4,4-difluoro-1,3-dimethyl-5-(4-methoxyphenyl)-4-bora-3α,4α-diaza-s-indacene-2-propionyl) amino)hexanoyl)-sn-glycero-3-phosphoethanolamine conjugated to a sulfo-diazirine moiety (compound 4)

According to yet another embodment, the invention provides process for preparation of photoactivable fluorescent lipid probe which process comprises; reacting lipid consisting fluorophore moiety with photoactivable moiety in a solvent at alkaline pH range of 7.0 to 9.0 for 10-20 hours at warm temperature conditions.

The lipid consisting fluorophore moiety according to the invention is selected from 1-palmitoyl-2-(dipyrrometheneboron difluoride) undecanoyl-sn-glycero-3-phosphoethanolamine or 1-oleoyl-2-(6-((4,4-difluoro-1,3-dimethyl-5-(4-methoxyphenyl)-4-bora-3α,4σ-diaza-s-indacene-2-propionyl)amino)hexanoyl)-sn-glycero-3-phosphoethanolamine.

The photoactivable moiety according to the invention is selected from with NHS-diazirine succinimidyl 4,4'-azipentanoate or succinimidyl 2-((4,4'-azipentanamido)ethyl)-1,3'-dithiopropionate.

In a further embodiment, the invention provides a method for proximity labelling-based identification of membrane-associated protein (PLIMAP), which method comprises;
  a) Incubating photoactivable fluorescent lipid probe incorporated into liposomes with desired protein in presence of DGS-NTA(Ni2+);
  b) Exposing the mixture of step 1 to UV (365 nm) for 1 min to activate the photoactivable diazirine group or sulfo-diazirine group in the lipid probe; followed by optionally treating with DTT to reduce the disulfide bond; and
  c) identifying the fluorescent membrane-associated protein/membrane-bound fraction that selectively cross-linked to the photoactivable fluorescent lipid due to proximity to the membrane, by fluorescence imaging of proteins resolved using SDS-PAGE.

As is evident from the above method, it can be concluded that the photoactivable fluorescent lipid probes of the present invention can efficiently work as a means to detect membrane binding of proteins for example, His-tagged Pfu.

In another embodiment, samples with the lipid probes containing liposomes but lacking DGS-NTA(Ni2+), when exposed to UV light showed no crosslinking emphasizing that stable membrane association is necessary for crosslinking to the fluorescent lipid probes of the present invention and not just random collision of proteins with liposomes.

Thus, the method for PLiMAP, as described in the present invention obviates the need of a high-speed centrifugation spin to separate the fraction of liposome-bound proteins that is otherwise a necessary step in traditional liposome-based sedimentation assay.

Accordingly, in an embodiment, the current invention provides a fluorescent 1-palmitoyl-2-(dipyrrometheneboron difluoride) undecanoyl-sn-glycero-3-phosphoethanolamine conjugated to a UV-activable diazirine moiety at the headgroup, hereafter referred to as Compound 1, which when incorporated into liposomes can crosslink with any MAP bound to these liposome upon UV exposure.

The crosslinked MAPs can then be detected on an SDS-PAGE method, which is referred as proximity labelling-based identification of membrane-associated protein (PLIMAP). This method is specifically adopted based on the premise that; (a) phospholipids comprise the bulk of lipids in cell membranes and any probe that is structurally similar to a phospholipid would mimic the bulk lipid in the membrane, (b) MAPs are by definition in close proximity to phospholipids in the membrane and upon incorporation of such a probe in the membrane would crosslink with MAPs in proximity following a short exposure to UV that activates the diazirine moiety, and (c) such fluorescent cross-linked MAPs can be visualized on an SDS-PAGE gel and later identified using mass spectrometry.

In another embodiment, the invention provides synthesis of Compound 1, which comprises reaction of 1-palmitoyl-2-(dipyrrometheneboron difluoride) undecanoyl-sn-glycero-3-phosphoethanolamine with NHS-diazirine succinimidyl 4,4'-azipentanoate in a solvent at alkaline pH for 10-20 hours at warm temperature (as shown in FIG. 1).

In another embodiment, the formation of Compound 1 generated through this reaction was confirmed by HRMS (FIG. 2) by achieving the experimental mass of 976.5899, which is in concurrence with the theoretical mass of 976.5917.

In another embodiment, the application of Compound 1 in identifying MAPs is demonstrated using a candidate protein, i.e., His-tagged Pfu. His-tagged proteins bind membranes that contain 1,2-dioleoyl-sn-glycero-3-[(N-(5-amino-1-carboxypentyl)iminodiacetic acid)succinyl] (ammonium salt), also known as DGS-NTA(Ni2+) lipid (Pucadyil and Holkar, Mol. Biol. Cell. (2016) 27:3156-3163).

Figure 3:
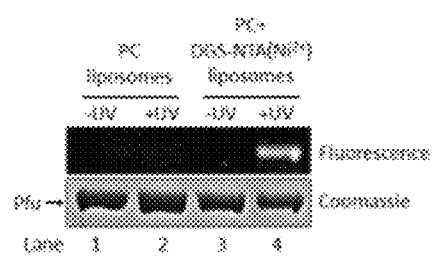
FIG. 3: Validation of Compound 1 in identifying MAPs. Compound 1 was incorporated into PC liposomes (lanes 1, 2) or PC liposomes with DGS-NTA(Ni2+) (lanes 3, 4) and mixed with His-tagged Pfu. Samples were either left unexposed (lanes 1, 3) or exposed (lanes 2, 4) to UV and resolved using SDS-PAGE. The gel was imaged directly for fluorescence to detect proteins crosslinked with Compound 1 and stained with Coomassie and imaged to detect total protein input in the reaction. Results reveal that His-tagged Pfu becomes crosslinked with Compound 1 and is therefore rendered fluorescent only upon UV exposure and provided liposomes contain DGS-NTA(Ni2+) (lane 4) but not under other conditions (lanes 1-3).

Accordingly, Compound 1 was incorporated at 1 mol % in (phosphatidylcholine) PC liposomes or PC liposomes with DGS-NTA(Ni2+) and mixed with His-tagged Pfu. Samples were either left unexposed or exposed to UV (365 nm) for 1 min to activate the diazirine group in Compound 1 and later resolved using SDS-PAGE. The gel was imaged on a fluorescent scanner (Syngene G Box), to detect proteins crosslinked with Compound 1, and subsequently stained with Coomassie dye and imaged to detect total protein input in the reaction. As can be seen in FIG. 3, His-tagged Pfu was rendered fluorescent by cross-linking with Compound 1 only with PC liposomes containing DGS-NTA(Ni2+) liposomes but not with PC liposomes alone or in the absence of UV exposure, thereby demonstrating the utility of Compound 1 to detect membrane-bound His-tagged Pfu.

In another embodiment, the present invention provides synthesis and validation of 1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine conjugated to UV-activable diazirine moiety at the headgroup, hereafter referred to as Compound 2. Accordingly, 1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine is reacted with succinimidyl 4,4'-azipentanoate in a solvent at alkaline pH for 10-20 hours under warm temperature conditions to form a conjugate, viz., Compound 2 (FIG. 4), which when incorporated into liposomes can cross-link with any MAP bound to these liposomes. Unlike Compound 1 that emits green fluorescence, Compound 2 emits red fluorescence. This will allow multiplexing in fluorescence-based detection in PLiMAP.

In another embodiment, the formation of Compound 2 generated through this reaction was confirmed by HRMS (FIG. 5) by achieving the experimental mass of 1081.5789, which is in concurrence with the theoretical mass of 1081.5768.

Figure 6:
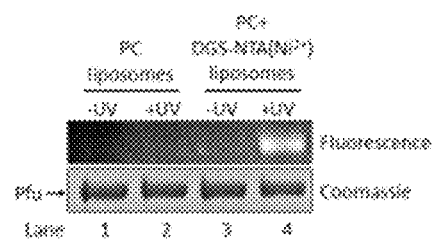
FIG. 6: Validation of Compound 2 in identifying MAPs. Compound 2 was incorporated into PC liposomes (lanes 1, 2) or PC liposomes with DGS-NTA($Ni^{2+}$) (lanes 3, 4) and mixed with His-tagged Pfu. Samples were either left unexposed (lanes 1, 3) or exposed (lanes 2, 4) to UV and resolved using SDS-PAGE. The gel was imaged directly for fluorescence to detect proteins crosslinked with Compound 2 and stained with Coomassie and imaged to detect total protein input in the reaction. Results reveal that His-tagged Pfu becomes crosslinked with Compound 2 and is therefore rendered fluorescent only upon UV exposure and provided liposomes contain DGS-NTA($Ni^{2+}$) (lane 4) but not under other conditions (lanes 1-3).

In yet another embodiment, the application of Compound 2 in identifying MAPs is demonstrated using His-tagged Pfu protein. Accordingly, Compound 2 was incorporated at 1 mol % in PC liposomes or PC liposomes with DGS-NTA (Ni2+) and mixed with His-tagged Pfu. Samples were either left unexposed or exposed to UV (365 nm) for 1 min to activate the diazirine group in Compound 2 and later resolved using SDS-PAGE. The gel was imaged on a fluorescent scanner (Syngene G Box), to detect proteins crosslinked with Compound 2, and subsequently stained with Coomassie and imaged to detect total protein input in the reaction. As can be seen in FIG. 6, His-tagged Pfu was rendered fluorescent by cross-linking with Compound 2 only with PC liposomes containing DGS-NTA(Ni2+) liposomes but not with PC liposomes alone or in the absence of UV exposure thereby demonstrating the utility of Compound 2 to detect membrane-bound His-tagged Pfu.

Figure 7:
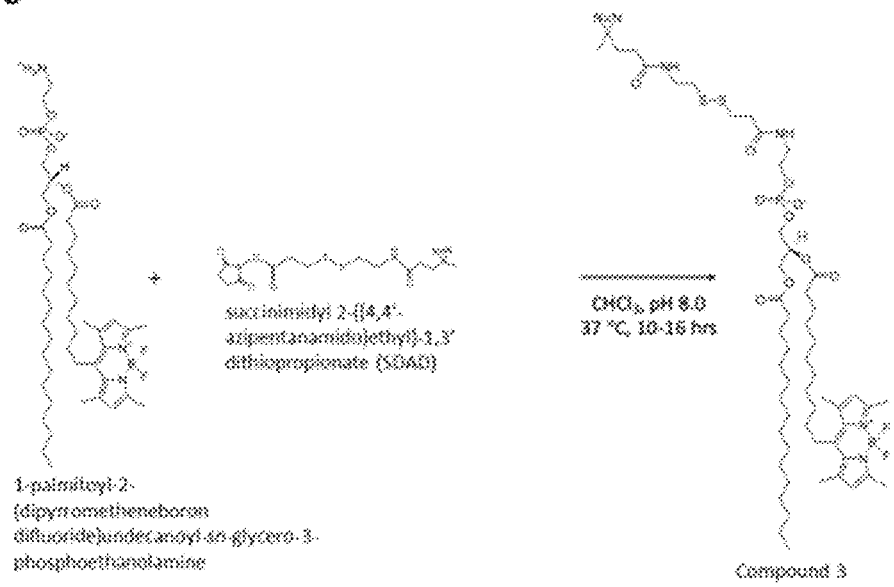
FIG. 7: Synthesis scheme for Compound 3.

In another embodiment, the present invention provides synthesis and validation of 1-palmitoyl-2-(dipyrrometheneboron difluoride) undecanoyl-sn-glycero-3-phosphoethanolamine conjugated to UV-activable sulfo-diazirine moiety at the head group, herein after referred as Compound 3. Accordingly, 1-palmitoyl-2-(dipyrrometheneboron difluoride) undecanoyl-sn-glycero-3-phosphoethanolamine is reacted with succinimidyl 2-((4,4'-azipentanamido)ethyl)-1,3'-dithiopropionate in a solvent at alkaline pH for 10-20 hours under warm temperature conditions to form a conjugate, viz., Compound 3 (FIG. 7).

Unlike the Compound 1 and compound 2 that form permanent crosslinks with MAPs, Compound 3 carries a disulfide bond between the diazirine moiety and the fluorescent phosphatidylethanolamine (referred to as adduct herein) such that addition of a reducing agent like DTT can cleave the disulfide bond and release the fluorescent adduct from the crosslinked MAP. This will render the MAP less hydrophobic which may facilitate mass spectrometric analysis thus further expanding the utility of PLiMAP.

In another embodiment, the formation of Compound 3 generated through this reaction was confirmed by HRMS (FIG. 8) by achieving the experimental mass of 1139.6056, which is in concurrence with the theoretical mass of 1139.6042.

Figure 9:
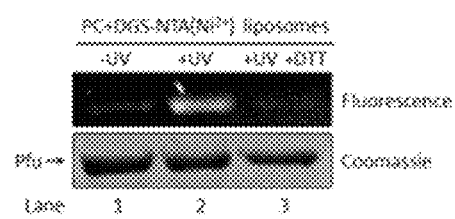
FIG. 9: Validation of Compound 3 in identifying MAPs and subsequent release of the fluorescent adduct from the crosslinked MAP. Compound 3 was incorporated into PC liposomes with DGS-NTA($Ni^{2+}$) and mixed with His-tagged Pfu. Samples were either left unexposed (lane 1) or exposed (lanes 2) to UV. A third sample was exposed to UV and then mixed with DTT (lane 3). Samples were resolved using SDS-PAGE. The gel was imaged directly for fluorescence to detect proteins crosslinked with Compound 3 and stained with Coomassie and imaged to detect total protein input in the reaction. Results reveal that His-tagged Pfu becomes crosslinked with Compound 3 and is therefore rendered fluorescent only upon UV exposure (lane 2). Importantly, addition of DTT cleaves the disulfide bond in Compound 3 thereby releasing the fluorescent adduct and rendering the crosslinked His-tagged Pfu non-fluorescent (lane 3).

In another embodiment, the application of Compound 3 in identifying MAPs and subsequent release of the fluorescent adduct from the crosslinked MAP is demonstrated using His-tagged Pfu protein. Accordingly, Compound 3 was incorporated at 1 mol % in PC liposomes with DGS-NTA (Ni2+) and mixed with His-tagged Pfu. Samples were either left unexposed, exposed to UV (365 nm) for 1 min to activate the diazirine group in Compound 3 or exposed to UV and treated with DTT' to reduce the disulfide bond in Compound 3 and later resolved using SDS-PAGE. The gel was imaged on a fluorescent scanner (Syngene G Box), to detect proteins crosslinked with Compound 3, and subsequently stained with Coomassie and imaged to detect total protein input in the reaction. As can be seen in FIG. 9, His-tagged Pfu was rendered fluorescent by cross-linking with Compound 3 only with PC liposomes containing DGS-NTA(Ni2+) and exposed to UV and that the subsequent addition of DTT causes dissociation of the fluorescent adduct thereby rendering the crosslinked His-tagged Pfu non-fluorescent.

Figure 10:
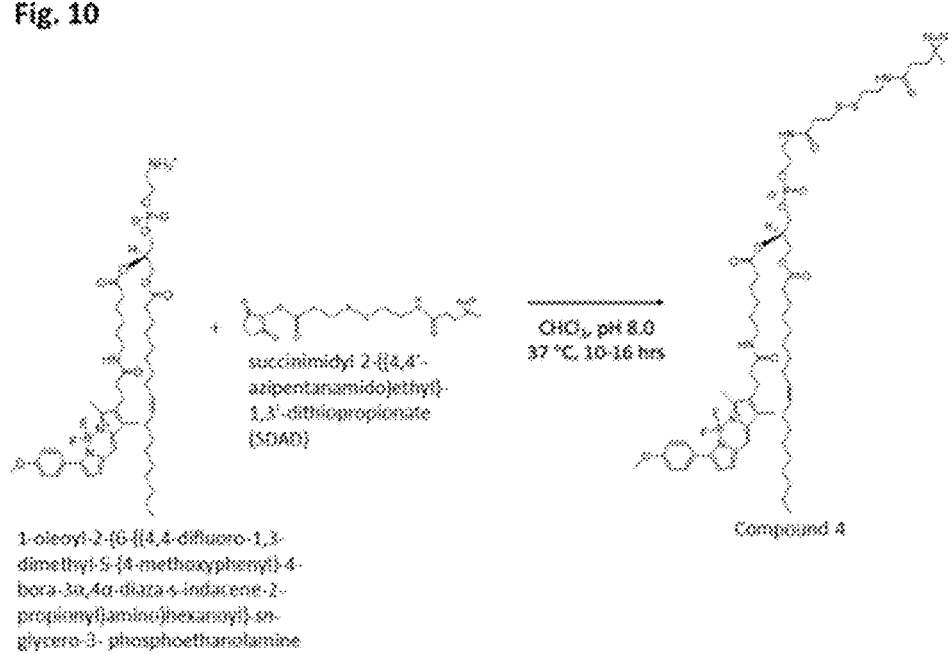
FIG. 10: Synthesis scheme for Compound 4.

In another embodiment, the invention provides synthesis and validation of 1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine conjugated to a sulfo-diazirine moiety, herein after referred as Compound 4. Unlike Compound 3, which emits green fluorescence, Compound 4 emits red fluorescence which will permit further multiplexing in fluorescence-based detection in PLiMAP. Accordingly, 1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine is reacted with succinimidyl 2-((4,4'-azipentanamido)ethyl)-1,3'-dithiopropionate in a solvent at alkaline pH for 10-20 hours under warm temperature conditions to form a conjugate, hereafter referred to as Compound 4 (FIG. 10).

Figure 11:
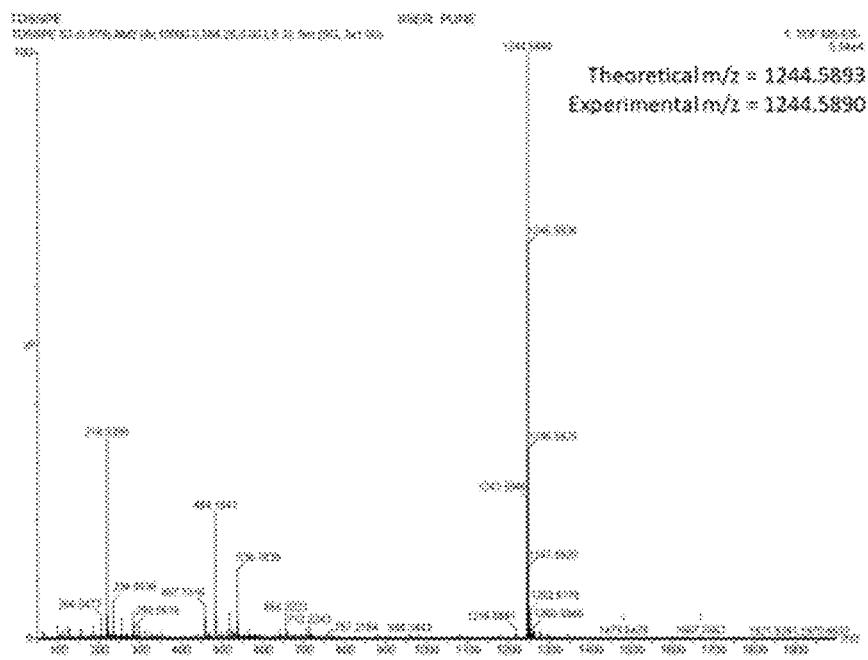
FIG. 11: HRMS characterization of Compound 4.

In another embodiment, the formation of Compound 4 generated through this reaction was confirmed by HRMS (FIG. 11) by achieving the experimental mass of 1244.5890, which is in concurrence with the theoretical mass of 1244.5893.

The following examples are presented to further explain the invention with experimental conditions, which are purely illustrative and are not intended to limit the scope of the invention.

EXAMPLES

Example 1: Synthesis of Compound 1

1-palmitoyl-2-(dipyrrometheneboron difluoride) undecanoyl-sn-glycero-3-phosphoethanolamine (0.28 micromoles) and NHS-diazirine succinimidyl 4,4'-azipentanoate (2.8 micromoles) were mixed in chloroform (0.1 ml) with triethanolamine (1.5 microliters) added to maintain pH 8.0 for 14 hours at 37° C. with stirring.

Figure 2:
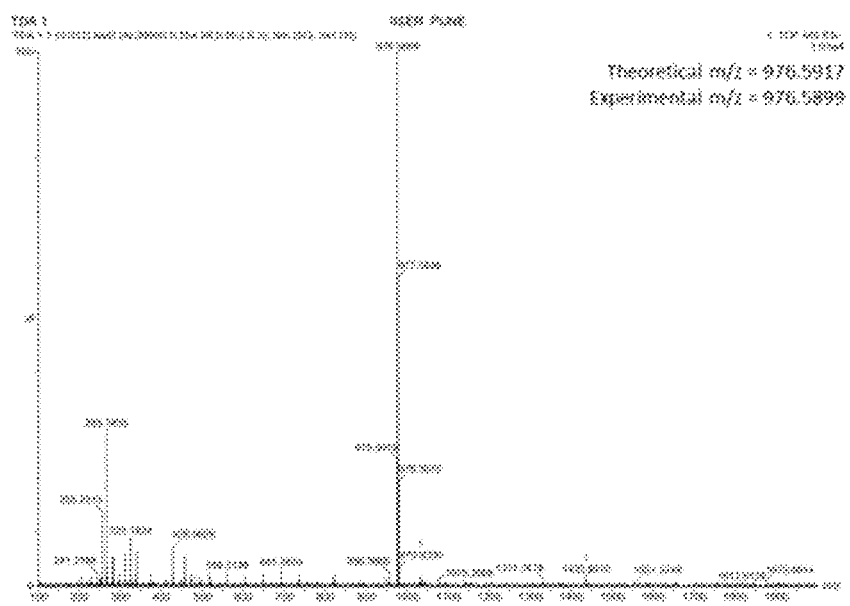
FIG. 2: HRMS characterization of Compound 1.

Compound 1 thus formed was isolated by thin-layer chromatography on silica gel using a solvent mixture of chloroform/acetone/methanol/acetic acid/water (9:2:1.6:1:0.5 v:v). The compound was extracted with chloroform from the silica gel, dried and analyzed using High Resolution Mass Spectrometry (HRMS). The experimental mass achieved is 976.5899 which is in concurrence with the theoretical mass of 976.5917, as shown in FIG. 2.

Example 2: Synthesis of Compound 2

Figure 4:
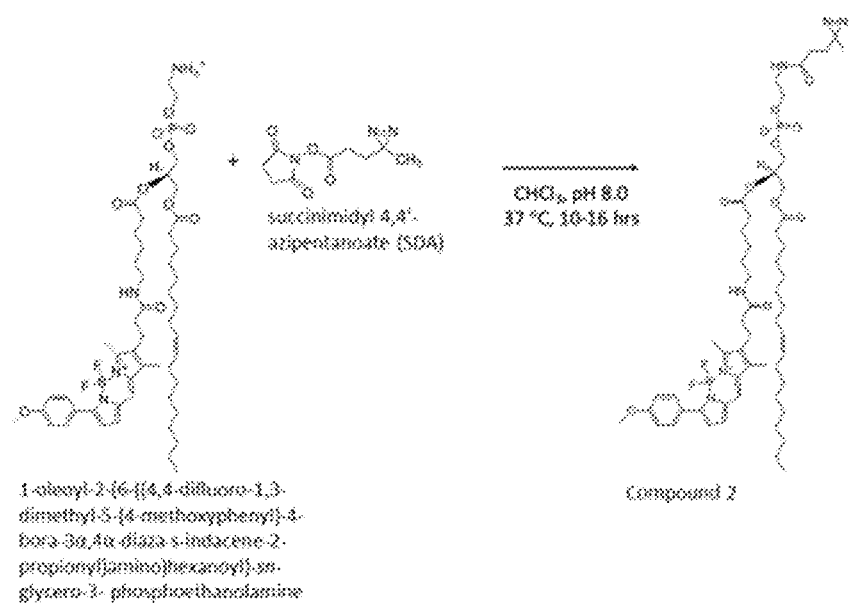
FIG. 4: Synthesis scheme for Compound 2.
Figure 5:
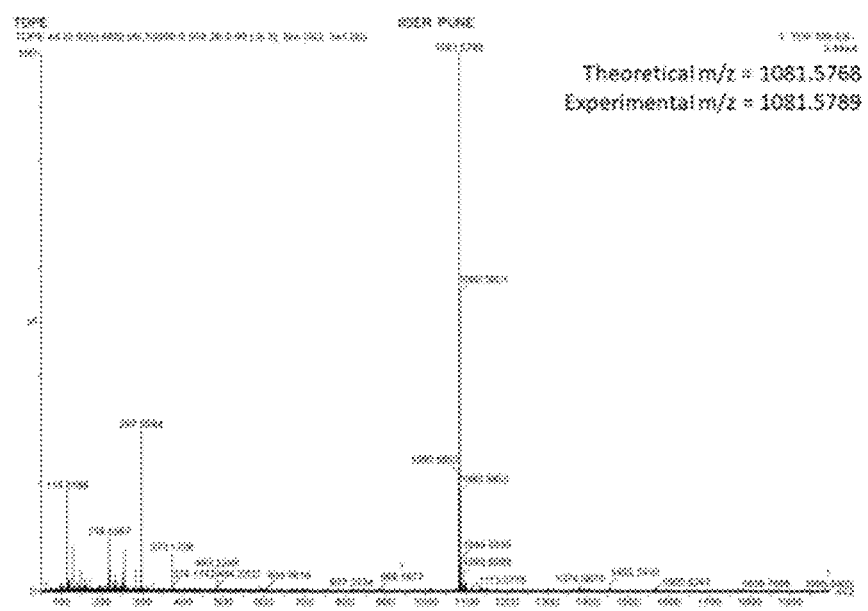
FIG. 5: HRMS characterization of Compound 2.

1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine (0.28 micromoles) and succinimidyl 4,4'-azipentanoate (2.8 micromoles) were mixed in chloroform (0.1 ml) with triethanolamine (1.5 microliters) added to maintain the apparent pH equal to 8.0 for 14 hours at 37° C. (FIG. 4). Compound 2 thus formed was isolated by thin-layer chromatography on silica gel using a solvent mixture of chloroform:acetone:methanol:acetic acid:water (9:2:1.6:1:0.5, v:v). Compound 2 was extracted with chloroform from the silica gel, dried and analyzed using High-Resolution Mass Spectrometry (HRMS). As shown in FIG. 5, the experimental mass determined is 1081.5789, which is in good agreement with the theoretical mass of 1081.5768.

Example 3: Synthesis of Compound 3

Figure 8:
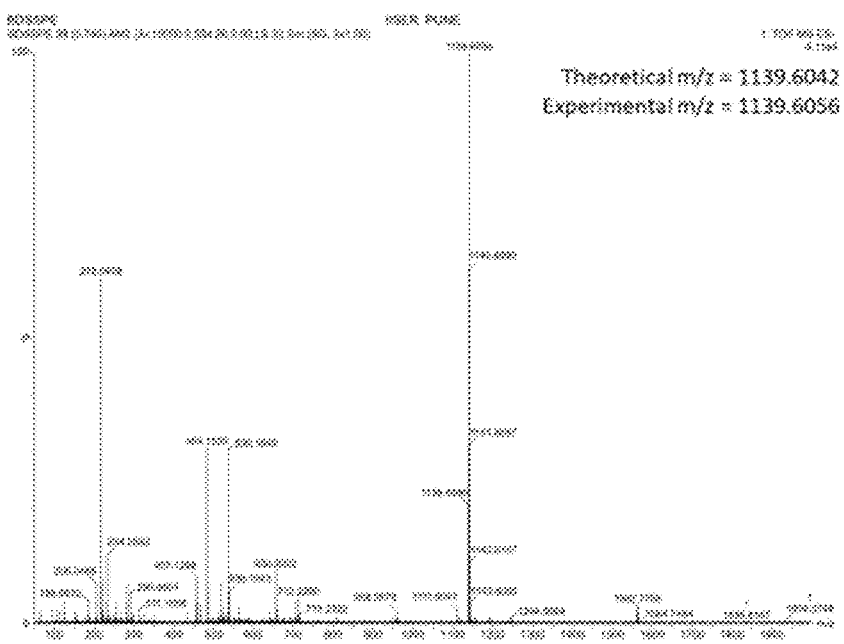
FIG. 8: HRMS characterization of Compound 3.

1-palmitoyl-2-(dipyrrometheneboron difluoride) undecanoyl-sn-glycero-3-phosphoethanolamine (0.28 micromoles) and succinimidyl 2-((4,4'-azipentanamido)ethyl)-1,3'-dithiopropionate) (2.8 micromoles) were mixed in chloroform (0.1 ml) with triethanolamine (1.5 microliters) added to maintain the apparent pH equal to 8.0 for 14 hours at 37° C. (FIG. 7). Compound 3 thus formed was isolated by thin-layer chromatography on silica gel using a solvent mixture of chloroform:acetone:methanol:acetic acid:water (9:2:1.6:1:0.5, v:v). The compound was extracted with chloroform from the silica gel, dried and analyzed using High-Resolution Mass Spectrometry (HRMS). As shown in FIG. 8, the experimental mass determined is 1139.6056, which is in good agreement with the theoretical mass of 1139.6042.

Example 4: Synthesis of Compound 4

1-oleoyl-2-(6-((4,4-difluoro-1,3-dimethyl-5-(4-methoxyphenyl)-4-bora-3α,4α-diaza-s-indacene-2-propionyl)amino)hexanoyl)-sn-glycero-3-phosphoethanolamine (0.28 micromoles) and succinimidyl 2-((4,4'-azipentanamido)ethyl)-1,3'-dithiopropionate)(2.8 micromoles) were mixed in chloroform (0.1 ml) with triethanolamine (1.5 microliters) added to maintain the apparent pH equal to 8.0 for 14 hours at 37° C. (FIG. 10). Compound 4 thus formed was isolated by thin-layer chromatography on silica gel using a solvent mixture of chloroform:acetone:methanol:acetic acid:water (9:2:1.6:1:0.5, v:v). The compound was extracted with chloroform from the silica gel, dried and analyzed using High-Resolution Mass Spectrometry (HRMS). As shown in FIG. 10, the experimental mass determined is 1244.5890, which is in good agreement with the theoretical mass of 1244.5893.

INDUSTRIAL ADVANTAGES

The proximity labelling-based identification of membrane-associated protein (PLIMAP) method described herein using Photoactivable fluorescent lipid probes does not necessitate separation of membrane-bound from free proteins and therefore simplifies the detecting MAPs. This process thus eliminates the requirement of an ultracentrifuge or other sophisticated apparatus such as NMR, SPR or a fluorescence microscope for detecting MAPs.

Therefore, PLiMAP method represents a considerably less tedious experimental workflow than any liposome-binding assay described till date.

Photoactivable fluorescent lipid probes can be synthesized in a single step chemical reaction with high yield from commercially available reagents.

This reaction is facile and does not require any specialized equipment and thus easier for industrial scale up.

What is claimed is:

1. A photoactivable fluorescent lipid probe, comprising:
    (a) a lipid moiety that is

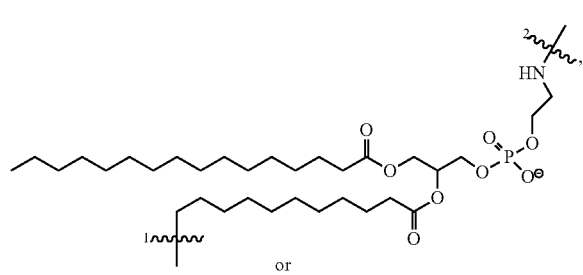

or

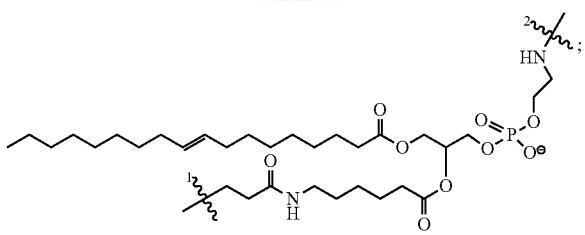

(b) a fluorophore moiety that is a dipyrrometheneboron difluoride group, and
    (c) a photoactivable moiety that is a diazirine group;
    wherein 1 ∽ represents point of attachment of the fluorophore moiety;
    wherein 2 ∽ represents point of attachment of the photoactivable moiety; and
    wherein the fluorophore and the photoactivable moiety are covalently attached to the lipid moiety.

2. The photoactivable fluorescent lipid probe as claimed in claim 1, wherein the dipyrrometheneboron difluoride group is selected from the group consisting of (4,4-difluoro-1,3-dimethyl-5-(4-methoxyphenyl)-4-bora-3a,4a-diaza-s-indacene-2-propionyl)amino group and 4,4-difluoro-1,3,5,7-tetramethyl-4-bora-3a,4a-diaza-s-Indacene group.

3. The photoactivable fluorescent lipid probe as claimed in claim 1, wherein the photoactivable moiety is directly connected to the lipid moiety.

4. The photoactivable fluorescent lipid probe as claimed in claim 1, wherein the photoactivable moiety is connected to the lipid moiety through a disulfide bond, which can be released from the lipid by reducing the disulfide bond.

5. A photoactivable fluorescent lipid probe, selected from the group consisting of:
    a) 1-palmitoyl-2-(dipyrrometheneboron difluoride) undecanoyl-sn-glycero-3-phosphoethanolamine, conjugated to a diazirine moiety at the terminal amine group of the phosphoethanolamine; and
    b) 1-oleoyl-2-(6-((4,4-difluoro-1,3-dimethyl-5-(4-methoxyphenyl)-4-bora-3α,4α-diaza-s-indacene-2-propionyl)amino) hexanoyl)-sn-glycero-3-phosphoethanolamine, conjugated to a diazirine moiety at the terminal amine group of the phosphoethanolamine.

6. A process for preparation of the photoactivable fluorescent lipid probe as claimed in claim 1, comprising:
    reacting a lipid comprising a fluorophore moiety with a photoactivable moiety in a solvent at an alkaline pH ranging between of 7.0 to 9.0 for 10-20 hours;
    wherein:
    the lipid comprising the fluorophore moiety is

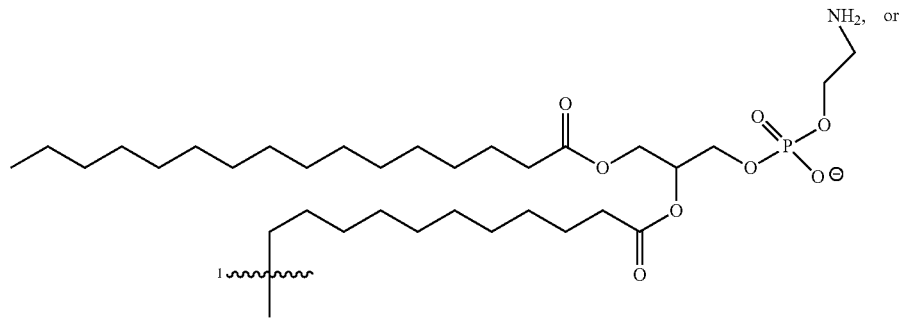

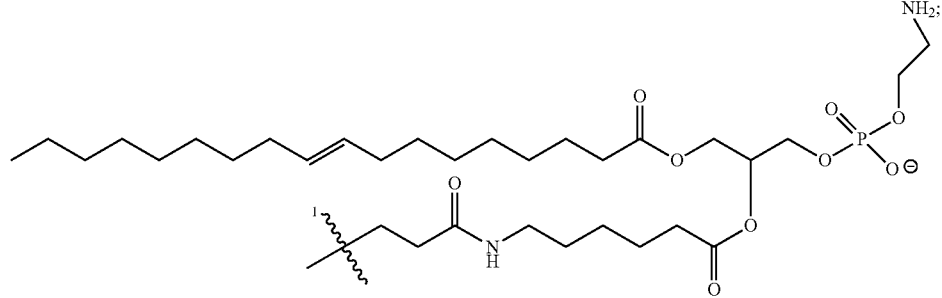

the fluorophore moiety is a dipyrromethaneboron difluoride group, and the photoactivable moiety is a hydroxysuccinimidyl ester comprising a diazirine group; and 1 〰 represents point of attachment of the fluorophore moiety.

7. The process as claimed in claim 6, wherein, the photoactivable moiety is:
   NHS-diazirine succinimidyl 4,4'-azipentanoate;
   succinimidyl 2-((4,4'-azipentanamido)ethyl)-1,3'-dithiopropionate; or a mixture thereof.

* * * * *